US008172841B2

United States Patent
Défossez

(10) Patent No.: US 8,172,841 B2
(45) Date of Patent: May 8, 2012

(54) INTRAMEDULLARY FIXATION DEVICE

(75) Inventor: Henri Défossez, Colombier (CH)

(73) Assignee: DePuy International Limited, Leeds (GB)

( * ) Notice: Subject to any disclaimer, the term of this patent is extended or adjusted under 35 U.S.C. 154(b) by 780 days.

(21) Appl. No.: 11/846,023

(22) Filed: Aug. 28, 2007

(65) Prior Publication Data
US 2008/0051790 A1 Feb. 28, 2008

(51) Int. Cl.
A61B 17/56 (2006.01)
A61B 17/58 (2006.01)
A61F 2/30 (2006.01)

(52) U.S. Cl. .......................... 606/64; 606/62
(58) Field of Classification Search .............. 606/62–64, 606/65–67
See application file for complete search history.

(56) References Cited

U.S. PATENT DOCUMENTS

| | | | |
|---|---|---|---|
| 1,814,858 A | 7/1931 | Rutter | |
| 4,612,920 A * | 9/1986 | Lower | 606/66 |
| 2004/0158249 A1 | 8/2004 | Roth et al. | |

FOREIGN PATENT DOCUMENTS

| | | |
|---|---|---|
| EP | 0486483 A | 5/1992 |
| EP | 0521600 A | 1/1993 |
| GB | 2209947 A | 6/1989 |
| WO | WO 03/015649 A | 2/2003 |
| WO | WO 2004/089232 A1 | 10/2004 |

OTHER PUBLICATIONS

PCT Search Report dated Jun. 2, 2006.
UK Search Report dated Aug. 19, 2005.
IPER dated Jun. 8, 2007.

* cited by examiner

Primary Examiner — Eduardo C Robert
Assistant Examiner — Christina Negrelli
(74) Attorney, Agent, or Firm — Victor C. Moreno

(57) ABSTRACT

An intramedullary fixation device for use with a bone comprising a proximal end, is provided. The fixation device includes a nail sized and configured to be inserted into an intramedullary channel of the bone, the nail having a generally laterally extending bore, an arm sized and configured to be located so that at least a portion of the arm extends through the bore of the nail along the neck of the bone when the device is implanted in the bone, the arm having a threaded portion at one end for fixation into the head of the bone. The device also includes a locking mechanism to prevent rotation of the arm relative to the nail, the locking mechanism configured to allow sliding of the arm through the bore, the locking mechanism configured to be located on the lateral side of the nail and the distal side of the bone when the arm is disposed within the bore.

20 Claims, 3 Drawing Sheets

INTRAMEDULLARY FIXATION DEVICE

BACKGROUND OF THE INVENTION

The present invention relates to an intramedullary fixation device for use in treating the fracture or breakage of a bone, especially for use in treating a proximal femoral fracture or breakage.

SUMMARY OF THE INVENTION

In order to treat a fracture or breakage, it is necessary to provide a fixation device which restricts relative movement between the two or more parts of the fractured bone. For example, to treat a fracture or breakage in the neck of a femur or humerus, it is necessary to restrict relative movement between the head and body of the femur or humerus. However, it can be important to allow movement of the head relative to the body along the axis of the neck to aid proper healing of the fracture or breakage.

Fixation devices for treating fractures in the neck of a bone typically contain a nail for insertion into the intramedullary channel of the body of the bone, and an arm for which extends along the neck into the head of the bone. The arm can slide through a bore within the nail, but is restricted from twisting about its axis by features of the nail and the arm where they engage one another.

The present invention provides an intramedullary fixation device which comprises a nail for extension into the intramedullary channel of the bone, and an arm for fixation into the head, wherein the arm is capable of sliding relative to the nail, generally along the axis of the neck of the bone, but is prevented from rotating relative to the nail, by a locking mechanism which is located at the point of engagement between the arm and the side wall of the nail.

Accordingly, in one aspect, the invention provides an intramedullary fixation device, comprising: a nail which can be inserted into the intramedullary channel of a bone, the nail having a generally laterally extending bore; an arm which can be located so that it extends through the bore of the nail, along the neck when the device is implanted in a bone, the arm having a threaded portion at one end for fixation into the head of the bone; and in which the nail and arm between them provide a locking mechanism to prevent rotation of the arm relative to the nail while allowing sliding of the arm through the bore, wherein the locking mechanism is located on the lateral side of the nail and the distal side of the arm, relative to the bone.

Access to the device to engage the locking mechanism is facilitated by the mechanism being location on the lateral side of the device. This can be accessed relatively easily through a lateral incision, especially compared with a locking mechanism which requires access to the proximal end of the femur as disclosed in EP-A-0257118. In addition, this can make it easier to view the locking mechanism to ensure that it is properly engaged so as to prevent rotation.

The fixation device of the invention has the advantage that the locking mechanism is located at a point on the device which provides easy access to the mechanism by a surgeon inserting the device in a patient. Typically, an incision will be made on the lateral side of a patient. Therefore, as the locking mechanism is located on the lateral side of the nail relative to the patient, it will be positioned on the same side in which the incision will be made. This will allow the surgeon to easily view the locking mechanism to ensure that it is properly engaged so as to prevent rotation of the arm. Also, if the locking mechanism is of the type which can be actuated by the surgeon to engage or release the locking mechanism, as it is located on the same side of the body as the incision, the surgeon will be able to easily access and hence actuate the locking mechanism. In particular, the surgeon can view and actuate the locking mechanism without the need to create another incision in the patient.

The fixation device of the invention also has the advantage that the locking mechanism does not adversely affect the structural integrity of the nail. As will be understood, when in use, the arm of the device can bear load due to the weight of the patient. This is especially true when the fixation device is used to treat a proximal femoral fracture. This load can tend to cause the arm to pivot about the nail at the point the arm extends through the bore in the nail, in a clockwise direction, when viewed from the anterior side of the patient. The nail prevents the arm from pivoting due to the wall of the bore acting against the arm. As will be understood, only the portions of the wall of the bore that are (a) on the lateral side of nail and on the proximal side of the arm, and (b) on the medial side of the nail and on the distal side of the arm, will act against the pivoting of the arm. As the locking mechanism is located on the lateral side of the nail and the distal side of the arm, relative to the femur, any reduction in strength of the nail and/or arm at that point will not reduce the load bearing capabilities of the fixation device.

Hereinafter, the invention and its advantages will be described with reference to the treatment of a proximal femoral fracture. However, it will be appreciated that the invention is not limited to such application, and can be used in the treatment of other fractures, for example in the treatment of a proximal humeral fracture.

The locking mechanism can provide a direct contact between the lateral side of the nail and the distal side of the arm so as to prevent rotation. The locking mechanism can be a locking component which provides the direct contact between the lateral side of the nail and the distal side of the arm. The locking component can be formed as one piece with the nail. The locking component can be formed as one piece with the arm. Preferably, the locking component is formed as a separate piece to both the nail and the arm, and can be received by one of the nail and the arm. Accordingly, preferably the locking mechanism is an insert which can be located between, and contact both, the lateral side of the nail and the distal side of the arm to prevent rotation. Preferably the locking mechanism does not contact the proximal side of the arm. Preferably, the locking mechanism contacts the distal side of the arm only. Preferably the locking mechanism does not contact the medial side of the nail. Preferably, the locking mechanism contacts the lateral side of the nail only.

The locking mechanism can comprise a groove provided in one of the arm and nail, and a nub provided on the other of the arm and nail which can protrude into the groove. Accordingly, when brought together, the nub and the groove will be located on the lateral side of the nail and on the distal side of the arm. The locking mechanism can comprise a number of grooves provided in one of the arm and nail, and a corresponding number of nubs provided on the other of the arm and nail which can protrude into their respective grooves. As will be understood, the number of nubs and the number of grooves need not necessarily be the same. For example, there can be provided more grooves than nubs.

Preferably, the groove is substantially straight so as to allow the nub to slide along the length of the groove. The length of the groove will be greater than the length of the nub taken along the longitudinal axis of the groove. Preferably, the ratio of the length of the groove to the length of the nub is at least two, more preferably at least four, especially preferably at least six, for example eight. Preferably, the length of the groove is at least 10 mm, more preferably 15 mm, especially preferably 20 mm, for example at least 25 mm. Preferably the width of the groove taken perpendicular to the longitudinal axis of the groove is at least 2 mm, more preferably at least 3 mm, especially preferably at least 4 mm.

It can be important to limit the amount by which the arm can slide through the nail. This is because, if the arm travels too far through the nail, the arm can cause damage to the tissue surrounding the bone. For example, in the treatment of a proximal femoral fracture or breakage, it can be preferable to restrict the amount by which the arm can slide through the nail to prevent the arm from extending too far through the neck and into the head. If the arm does extend too far, then the head of the bone can be damaged, and in some circumstances the arm can penetrate the acetabulum of the joint, causing damage to it and surrounding tissue. Preferably, the length of the groove is not more than 90 mm, more preferably not more than 50 mm, especially preferably not more than 40 mm, for example not more than 30 mm.

Preferably the groove is closed off at its ends. The depth of the groove can be constant between its ends. Optionally, the depth of the groove can vary along its length. This can provide a way of increasing the resistance to the movement of the arm through the nail as the arm slides through the nail in a direction away from the shallow end of the groove. For example, the depth of the groove can be shallower towards its end that is distal to the threaded portion of the arm when the fixation device is assembled. As the arm slides through the nail in a direction away from the shallow end of the groove, the arm will be progressively wedged between the nub and walls of the bore. The greater the extent of such sliding, the greater the resistance to the sliding provided by the wedging of the arm.

Preferably, the depth of the groove becomes gradually shallower from its end proximal the threaded portion of the arm, towards its distal end. Preferably, the depth of the groove decreases monotonically from its proximal end to its distal end. Preferably, the depth of the groove decreases at a constant rate from its proximal end to its distal end. This can help to ensure that the increase in the resistance to the sliding of the arm increases proportionally to the extent of sliding.

The width of the nub taken in the direction perpendicular to the longitudinal axis of the groove should be small enough so as to fit within the groove, but large enough so as to prevent relative movement between the groove and the nub in the direction perpendicular to the longitudinal axis of the groove.

Preferably, the side wall of the nub is rounded (when viewed along its length). Preferably, the groove will have a corresponding cross sectional profile to receive the nub. Preferably, the shape and dimensions of the cross sectional profiles of the nub and groove are configured so that the nub is a snug fit within the groove. It can be preferable to provide a nub having a rounded side wall, so as to aid the location of the nub in the groove during assembly of the fixation device. Nevertheless, it will be appreciated that other shaped nubs and grooves can be used. For example, the cross sectional profiles of the nub and groove can be square or triangular.

Preferably, the groove is provided in the arm and the nub is provided on the nail. This can be advantageous as it can allow for a greater amount of sliding of the arm through the bore in the nail. This is because, the amount by which the arm can slide through the bore can be restricted by the length of the groove and the width of the nub. The groove can be longer on the arm due to the length of the arm being greater than the length of the bore in the nail. Preferably, the length of the groove is at least 5% of the length of the arm, more preferably at least 10%, especially preferably at least 15%, for example at least 20%. Preferably, the length of the groove is no greater than 60% of the length of the arm, more preferably no greater than 30%, especially preferably no greater than 25%, for example no greater than 20%.

Preferably, the nub can be displaced between a locked position in which the nub protrudes into the groove, and a release position in which the nub does not protrude into the groove, in order to allow insertion and removal of the arm from the nail. This can be advantageous as it allows the use of different arms with the same nail. Further, such configuration allows the removal of an arm so as to increase the ease of cleaning the different components of the fixation device.

It can be preferable for the nub to be a part of the arm or nail, wherein the nub is preassembled in the arm or nail, and wherein the nub can move relative to the arm or nail of which it is a part. This can help to ensure that a separate component is not required to be inserted into the fixation device so as to provide the locking mechanism. This can aid assembly as a surgeon need only to insert the arm through the bore in the nail, and then co-locate groove and nub and then displace the nub into its locked position.

The nub can be configured so that it can be retained in its released position without the need to apply force external to the fixation device to it. For example, the arm or nail on which the nub is located can provide a catch or latch mechanism for retaining the nub in its released position. Alternatively, the nub can be configured so that it is biased towards its locked position and is free to return to its locked position upon removal of an external force. For example, the nub can be mounted on a spring mechanism which can be compressed so as to displace the nub towards its released position. The spring loading mechanism can be provided by way of a spring or resiliently deformable material, such as an elastic material, or a shape memory alloy. The nub itself can be resiliently deformable so that it can be deformed into a released position upon the application of an external force and in which the nub returns to its original shape, so that the nub is in its locked position, upon the removal of the external force. For example, the nub can be made of an elastic material, or a shape memory alloy.

Preferably, the nub is removed from the nail and arm when in the release position, and displacement to the locked position involves locating the nub in a recess. The nub can be retained within the arm or nail by means of a retaining mechanism, which can be actuated so as to releasably fasten the nub to the arm or nail. The retaining mechanism can be a catch or latch mechanism. Preferably, the nub is a screw which can be partially captured within the arm or nail. More preferably, the nub is a grub screw which can be partially captured within a threaded recess in the arm or nail. The non-captured part of the screw or grub screw can protrude into the groove on the other of the arm or nail, when the device is assembled. It can be particularly advantageous to use a grub screw as they do not contain a large diameter head which therefore means that the entire length of the grub screw can be threaded and thereby utilise the entire length of the screw for securing the nub in the nail or arm. Also, as a grub screw is headless, this can increase the compactness of the fixation device as the grub screw can be fitted to be flush with the external surfaces of the nail or arm.

Preferably, the grub screw is in contact with the wall of the recess around at least 55% of its circumference. This has been found to be the optimum balance between ensuring that the grub screw is sufficiently retained within the recess and that the grub screw protrudes sufficiently into the groove when the fixation device is assembled so as to prevent rotation of the arm relative to the nail. It will be appreciated that the grub screw can be in contact with more or less of the recess around its circumference. For example, the percentage of circumference of the grub screw that is in contact within the wall of the recess can be in the range of 55% to 90%, more preferably 60% to 80%.

Preferably, a local restriction is built into the thread of the recess, which is deformed by the grub screw when the grub screw threadingly engages the recess, so as to resist rotation of the grub screw within the recess. This can be advantageous as it can help to prevent the grub screw from loosening, and thereby becoming unfastened from its engagement in the recess. Therefore, the provision of the local restriction in the thread of the recess can help to lock the grub screw in the recess. Preferably, the local restriction is made of the same material as the body in which the recess is provided.

Accordingly, in another aspect, the invention provides an intramedullary femoral fixation device, comprising: a nail which can be inserted into the intramedullary channel of a femur, the nail having a generally laterally extending bore; an arm which can be located so that it extends through the bore of the femoral nail, along the femoral neck when the device is implanted in a femur, the arm having a threaded portion at one end for fixation into the head of the femur; and in which the arm has a groove formed in it towards its end distal to the threaded portion, and the nail has a recess formed in its side wall, and in which the recess can receive a nub so that the nub can slide in the groove, allowing the arm to slide relative to the nail.

The fixation device of the invention has the advantage that the nub and groove between them provide a locking mechanism so as to prevent rotation of the arm relative to the nail while still allowing sliding of the arm through the bore. The provision of the recess in the side wall of the nail can increase the ease by which the fixation device is assembled. This is because, an incision typically will be made in a patient on the side of a patient. The nub can be easily inserted therefore into the recess if the incision and recess are co-located on the same side of the patient. Also, the use of a nub that can be inserted in the side wall of the nail can increase the simplicity of manufacture, assembly and disassembly of such fixation devices by removing the need for other more complicated locking mechanisms such as those that extend down the central channel of the nail.

Preferably, the nub and groove are located either on the lateral side of the nail and the distal side of the arm, or on the medial side of the nail or the small side of the arm. Such configurations have been found to improve the load bearing capabilities of the fixation device as compared to fixation devices in which the nub and groove are located on other sides of the nail and arm.

Preferably, the nub is a grub screw, and the recess has a corresponding thread for threaded engagement with the grub screw.

Preferably, the recess includes a stop to prevent the travel of the nub through the bore. For example, the stop can be provided by an end wall of the recess. Accordingly, preferably the recess extends only part way along the length of the bore.

The fixation device will generally be made from metallic based materials which are conventionally used in the manufacture of surgical instruments. Certain stainless steels can be particularly preferred.

BRIEF DESCRIPTION OF THE DRAWINGS

Embodiments of the present invention will now be described by way of example only with reference to the accompanying drawings in which:

FIG. 1b is a close up view of the locking mechanism of the fixation device shown in FIG. 1a;

FIG. 2a is a close up view of an alternative locking mechanism of the fixation device shown in FIG. 1a.

Referring to the drawings, FIG. 1a shows an intramedullary fixation device 2 suitable for the treatment of a proximal femoral fracture or breakage. The fixation device can be used to prevent relative movement between the head and body of a femur (not shown) during treatment of a fracture or breakage in the neck of the femur. As will be appreciated, the invention can also be used in the treatment of other fractures of a bone, for example the treatment of a proximal humeral fracture. The fixation device 2 generally comprises a nail 4 which can be inserted into the intramedullary channel of a femur. The nail includes a generally laterally extending bore 6. The fixation device 2 further generally comprises an arm 8 which can extend through the bore 6 of the nail 4, and which can extend through the femoral neck of a femur. The nail 4 and arm 8 between them provide a locking mechanism generally designated by reference numeral 10, located on the lateral side of the nail and the distal side of the arm relative to the femur into which the fixation device is inserted.

Figure 1A:
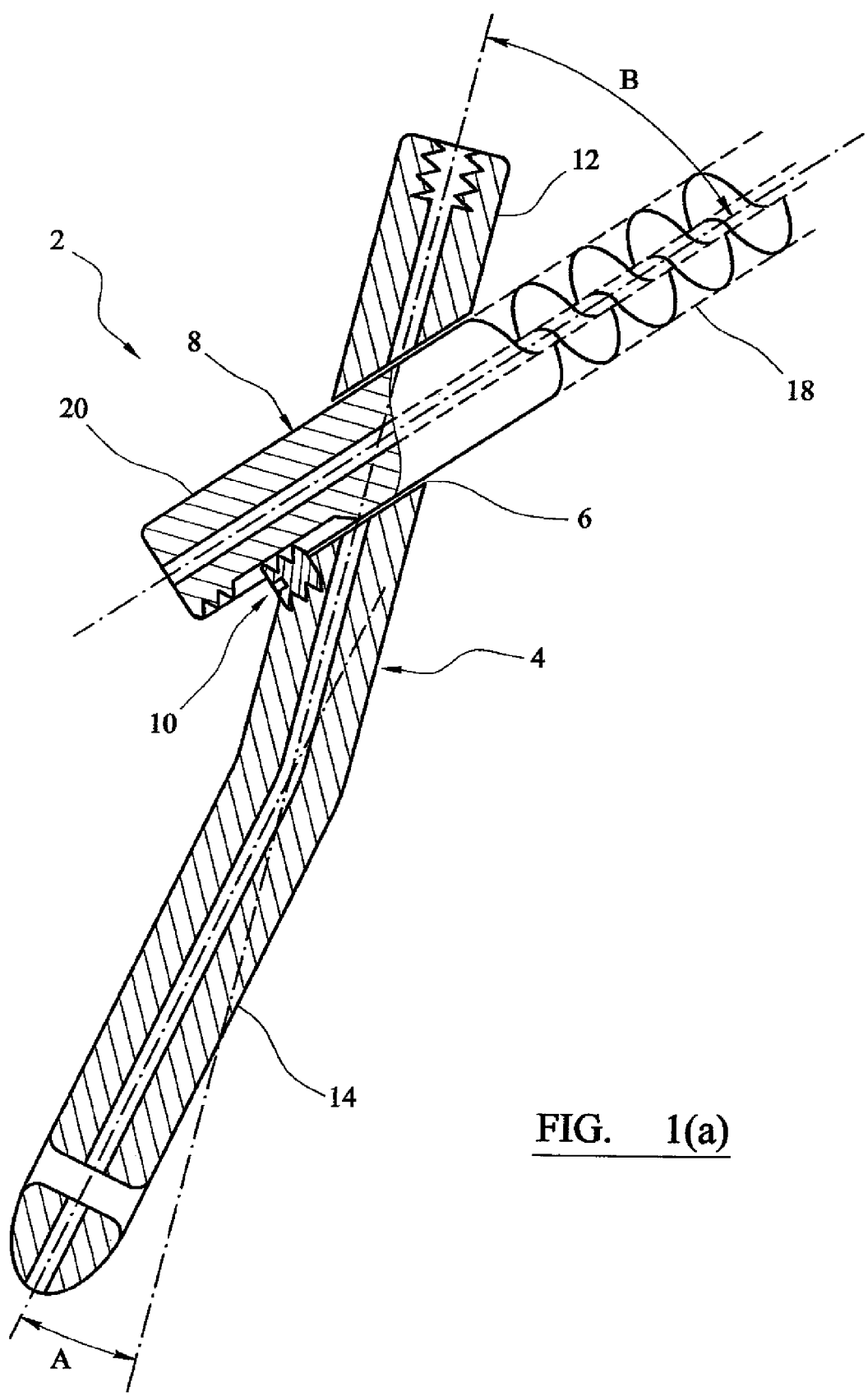
FIG. 1a is a schematic cross sectional side view of an intramedullary fixation device according to the present invention.

The nail 4 comprises a first substantially straight portion 12 and a second substantially straight portion. When in use, the first portion 12 of the nail 4 will be located towards the proximal end of the femur. The first and second portions are configured so that their longitudinal axes intersect each other at an angle A. In the embodiment shown, angle A is approximately 7", however it will be appreciated that the angle A can be any angle between 0" and 45", and especially any angle between 5° and 10°. The bore 6 is provided in the first portion 12 of the nail 4. The bore 6 extends through the first portion 12 of the nail 4 so that the angle B between the longitudinal axis of the bore and the longitudinal axis of the first portion is approximately 55". However, it will be appreciated that the angle B can be any angle between 10" and 135", and especially any angle between 25° and 90°. The nail 4 is cannulated. The cross sectional shape taken perpendicular to the length of the nail 4 is generally circular. The nail 4 is slightly tapered so that the diameter of the nail at its distal end (relative to the femur) is smaller than its diameter at its proximal end (relative to the femur).

The arm 8 has a substantially cylindrical shank portion 20 at a first end and a threaded portion 18 at its second end for fixation into the head of the femur. The diameter of the shank portion 20 that extends from the first end of the arm 8 towards the threaded portion 18 is sized so that it is slightly smaller than the diameter of the bore 6 in the nail 4 so that the arm can be received within the bore and slide within the bore, but is large enough to prevent the shank portion 20 from moving within the bore in a direction perpendicular to its longitudinal axis. The arm 8 is cannulated.

Figure 1B:
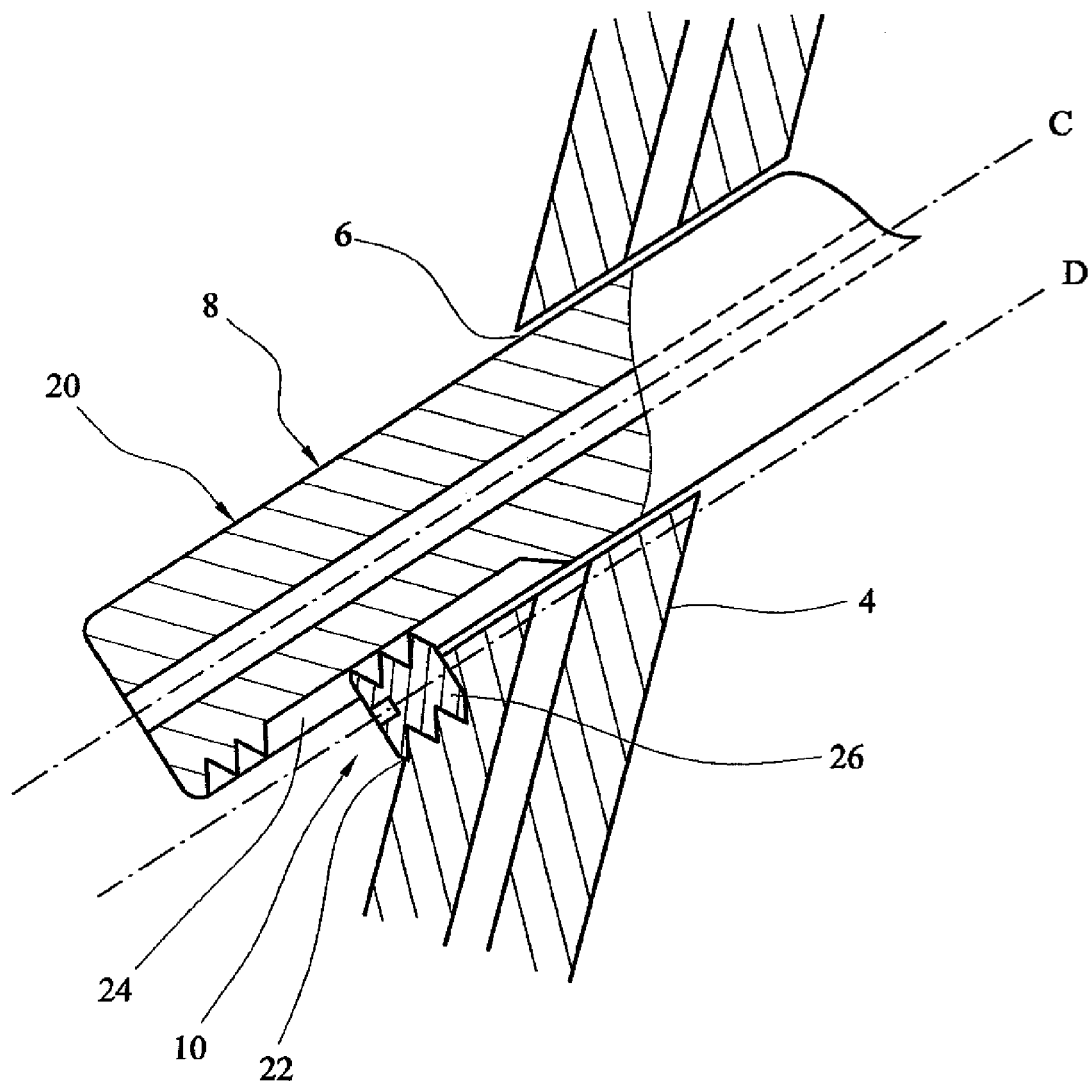

The locking mechanism provided by the nail 4 and the arm 8 is described in more detail in relation to FIG. 1b. As shown, the nail 4 has a recess formed in its side wall. The side wall of the recess 22 is threaded. The recess 22 is open in that at least a portion of the circumferential side wall of the recess is missing (so that the recess is exposed to the bore 6). The longitudinal axis of the recess is parallel to the longitudinal axis of the bore 6.

The shank portion 20 of the arm 8 includes a groove 24 formed as a depression in the circumferential surface of the arm. The groove 24 is located towards the end of the arm 8 distal to the threaded portion 18. The groove extends for approximately 25% of the length of the arm 8. The cross sectional shape and size of the groove 24 is constant along its length.

The locking mechanism 10 further comprises a grub screw 26 which can be received by the threaded recess. The grub screw 26, recess 22 and groove 24 are shaped and sized so that when assembled, a portion of the grub screw protrudes out of the open side of the recess into the groove. In the embodiment shown, approximately 75% of the circumference of the grub screw 26 is in contact with the wall of the recess 22. The recess 22, grub screw 26 and groove 24 are shaped and sized so as to allow movement of the arm 8 along its longitudinal axis to prevent rotation of the arm about its longitudinal axis. As illustrated, the axis C of the bore 6 and the axis D of the recess 22 within which the grub screw 26 is received are parallel.

Figure 2A:
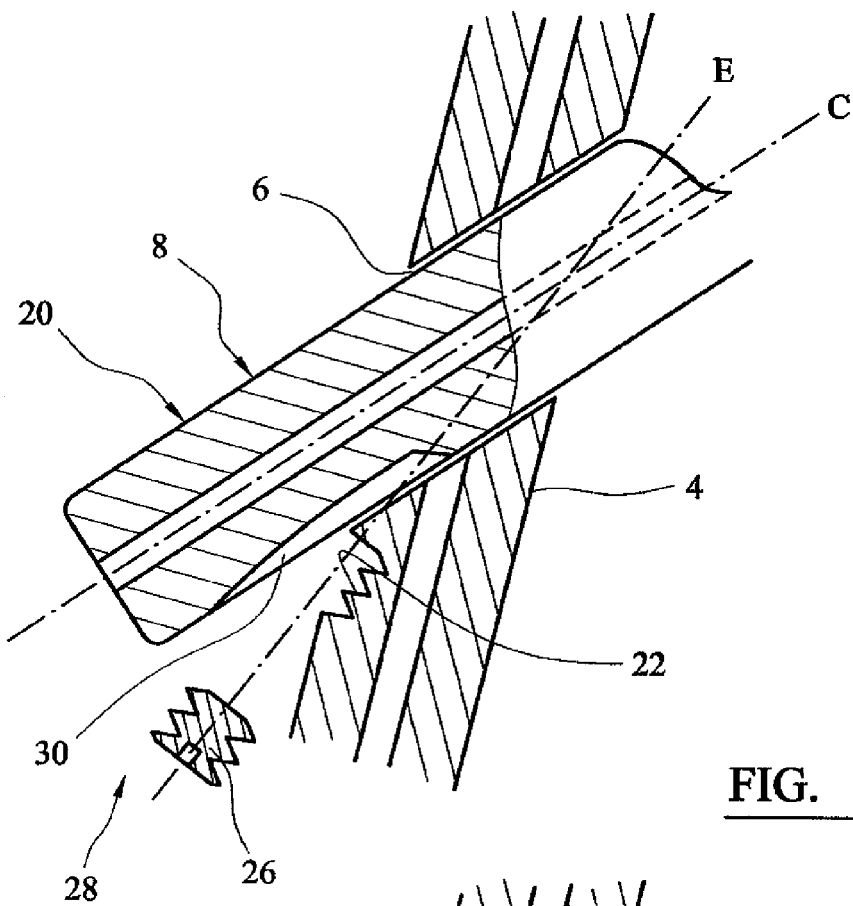
Figure 2B:
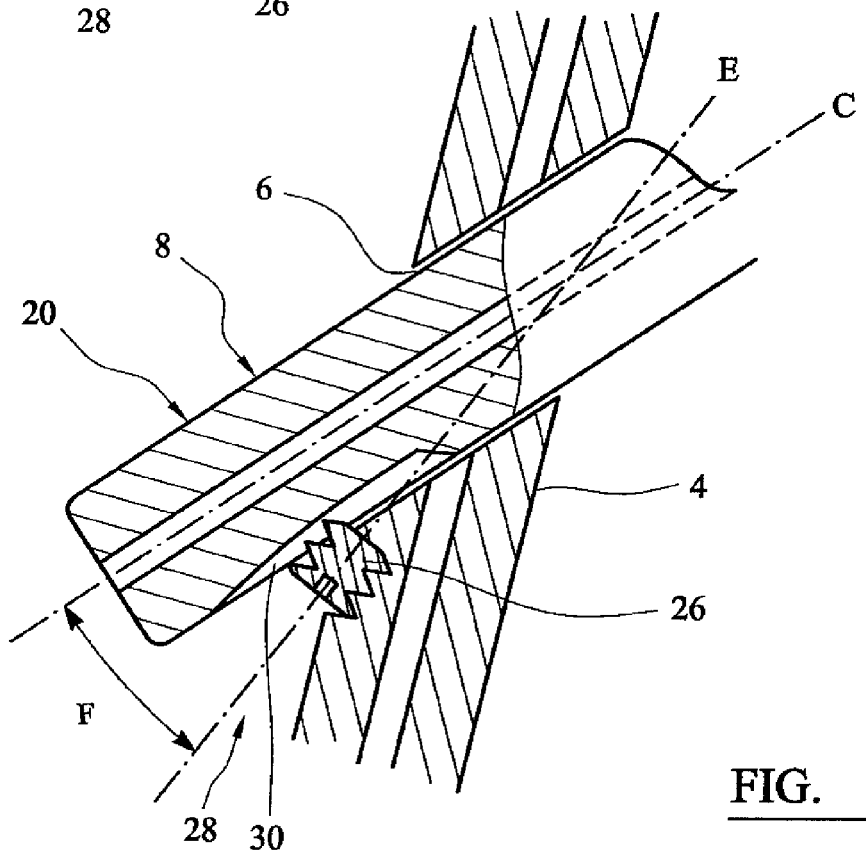
FIG. 2b is a close up view of the alternative locking mechanism shown in FIG. 2a wherein the grub screw has been received within the recess.

With reference to FIGS. 2a and 2b there is shown an alternative embodiment of the locking mechanism 28 according to the present invention. As shown, the depth of the groove 30 varies along its length. In particular, the groove 30 becomes progressively shallower towards its end distal to the threaded portion 18 of the arm 8. When the arm 8 is initially located in the bore 6, the grub screw 26 can be received in the groove 30 so that it is located at the deep end of the groove. In this position, the grub screw 26 is a snug fit within the groove 30. As the arm 8 slides through the bore 6 towards the head of the femur (not shown) the depth of the groove 30 at the point the grub screw 26 is located within the groove, decreases. As a result, the groove 30 becomes too shallow in order to fully receive the protruding part of the grub screw 26. Accordingly, the interaction between the groove 30 and the grub screw 26 tries to push the arm 8 away from the grub screw. However, such movement of the arm is restricted by the engagement of the part of the side wall of the arm 8 opposite to the groove 30 and grub screw 26 with the walls of the bore 6. As a result, the arm 8 become wedged within the bore 6, and sliding of the arm through the bore towards the head of the femur is restricted.

As shown, the axis C of the bore 6 and the axis E of the recess 22 within which the grub screw 26 is received are not parallel. This has been found to aid insertion of the grub screw 26 into the recess 22 when the depth of the groove 30 is shallower towards its distal end. In the embodiment shown, the angle F between the axes D, E is approximately 25°. However, it will be understood that this need not be the case. For example, the angle F can be any angle between 0° (i.e. the axes can be parallel) and 80°.

The invention claimed is:

1. An intramedullary fixation device for use with a bone having a proximal end, including a head, an intramedullary channel, a distal end, and a neck, comprising:
   a nail having a first portion having a longitudinal axis, at least a portion of the first portion being sized and configured to be located in the intramedullary channel such that the longitudinal axis is aligned within the intramedullary channel when in use, the nail having a lateral side and a generally laterally extending bore;
   an arm sized and configured to be located in the bore of the nail so that at least a first portion of the arm extends from one side of the bore and a second portion of the arm extends from the other side of the bore, the arm having a threaded portion at one end for fixation into the head of the bone; and
   a locking mechanism to prevent rotation of the arm relative to the nail, the locking mechanism comprising a groove provided in one of the arm and/or nail, and a nub provided on the other of the arm and nail that can protrude into the groove, the nub configured to slide in the groove thereby allowing the arm to slide relative to the nail, the locking mechanism configured to be located on the lateral side of the nail and the distal portion of the bone when the arm is disposed within the bore.

2. The intramedullary fixation device of claim 1, wherein the groove is provided in the arm and the nub is provided on the nail.

3. The intramedullary fixation device of claim 2, wherein the nub can be displaced between a locked position wherein the nub protrudes into the groove, and a released position wherein the nub does not protrude into the groove to allow insertion and removal of the arm from the nail.

4. The intramedullary fixation device of claim 2, wherein the nub is a separate piece to the arm or the nail, and can be fitted into and subsequently removed from a recess provided on the arm or nail so as to allow insertion and removal of the arm from the nail.

5. The intramedullary fixation device of claim 4, wherein the recess is threaded and the nub is a screw configured to threadingly engage the threaded recess.

6. The intramedullary fixation device of claim 5, wherein the screw is in contact with the wall of the recess around at least 55% of its circumference.

7. The intramedullary fixation device of claim 5, wherein a local restriction is built into the thread of the recess and is configured to be deformed by the screw when the screw threadingly engages the recess so as to resist rotation of the screw within the recess.

8. The intramedullary fixation device of claim 1, wherein the bore has a bore axis and the bore axis intersects the longitudinal axis of the nail.

9. An intramedullary fixation device, comprising:
   a nail having a first portion having a longitudinal axis, at least a portion of the first portion being sized and configured to be located in the intramedullary channel of a bone such that the longitudinal axis is aligned within the intramedullary channel when in use, the nail having a side wall and a generally laterally extending bore;
   an arm configured to be at least partially disposed within and through the bore of the nail so that at least a first portion of the arm extends from one side of the bore and a second portion of the arm extends from the other side of the bore, the arm having a threaded portion at one end or fixation into the head of the bone; and
   wherein the arm has a groove formed therein at a location proximal to the threaded portion, and the nail has a recess formed in the its side wall, and wherein the recess is configured to can receive a nub, the nub being configured to slide in the groove.

10. The intramedullary fixation device of claim 9, wherein at least 55% of the perimeter of the nub extends into the groove.

11. The intramedullary fixation device of claim 9, wherein the nub and groove are located either on the lateral side of the nail and the distal portion of the arm, or on the medial side of the nail and the proximal side of the arm.

12. The intramedullary fixation device of claim 9, wherein the nub is a screw, and the recess has a corresponding thread for threaded engagement with the screw.

13. The intramedullary fixation device of claim 9, wherein the nub is a separate piece from the arm or the nail, and the nub is configured to be fitted into and subsequently removed from the recess so as to allow insertion and removal of the arm from the nail.

14. An intramedullary fixation device for use with a bone having a proximal end, including a head, an intramedullary channel, a distal portion, and a neck, comprising:
- a nail having a first portion having a longitudinal axis, at least a portion of the first portion being sized and configured to be located in the intramedullary channel of a bone such that the longitudinal axis is aligned within the intramedullary channel when in use, the nail having a lateral side and a generally laterally extending bore;
- an arm sized and configured to be located in the bore of the nail so that at least a first portion of the arm extends from one side of the bore and a second portion of the arm extends from the other side of the bore, the arm having a threaded portion at one end for fixation into the head; and
- a locking mechanism comprising a groove provided in one of the arm and the nail, and a nub provided on the other of the arm and the nail, the nub being configured to protrude into the groove and slide therein thereby allowing the arm to slide relative to the nail, the locking mechanism being located on the lateral side of the nail and at a distal portion of the bone when the arm is disposed within the bore.

15. The intramedullary fixation device of claim 14, wherein the arm has the groove and the nub is provided on the nail.

16. The intramedullary fixation device of claim 14, wherein the nub is displacable between a locked position, where the nub protrudes into the groove, and a released position, where the nub does not protrude into the groove to allow insertion and removal of the arm from the nail.

17. The intramedullary fixation device of claim 14, wherein the nub is a separate piece from the arm or the nail, and the nub is configured to be fitted into and subsequently removed from a recess provided on the arm or the nail so as to allow insertion and removal of the arm from the nail.

18. The intramedullary fixation device of claim 17, wherein the recess is threaded and the nub is a screw configured to threadingly engage the threaded recess.

19. The intramedullary fixation device of claim 18, wherein the screw is in contact with the wall of the recess around at least 55% of its circumference.

20. The intramedullary fixation device of claim 18, wherein a local restriction is built into the thread of the threaded recess and is configured to be deformed by the screw when the screw threadingly engages the recess so as to resist rotation of the screw within the recess.

* * * * *